US008901330B2

(12) United States Patent
Doyle et al.

(10) Patent No.: US 8,901,330 B2
(45) Date of Patent: Dec. 2, 2014

(54) METHOD FOR PRODUCTION OF BIOFUEL

(75) Inventors: Michael Phillip Doyle, Carmel, CA (US); Steve Smith, Richmond, CA (US)

(73) Assignee: Sauber LLC, Emeryville, CA (US)

( * ) Notice: Subject to any disclaimer, the term of this patent is extended or adjusted under 35 U.S.C. 154(b) by 0 days.

(21) Appl. No.: 12/200,809

(22) Filed: Aug. 28, 2008

(65) Prior Publication Data

US 2009/0062559 A1   Mar. 5, 2009

Related U.S. Application Data (60) Provisional application No. 60/968,855, filed on Aug. 29, 2007.

(51) Int. Cl.

| | | |
|---|---|---|
| C11C 3/10 | (2006.01) | |
| C11C 3/00 | (2006.01) | |
| C07C 67/02 | (2006.01) | |
| B01D 17/02 | (2006.01) | |
| C07C 67/03 | (2006.01) | |
| C07C 67/48 | (2006.01) | |
| B01D 21/26 | (2006.01) | |
| C08G 63/78 | (2006.01) | |

(52) U.S. Cl.
CPC ............... *C11C 3/003* (2013.01); *C07C 67/02* (2013.01); *B01D 17/0208* (2013.01); *B01D 21/26* (2013.01); *C07C 67/03* (2013.01); *C07C 67/48* (2013.01); *C08G 63/78* (2013.01); *C10G 2300/1011* (2013.01); *Y02E 50/13* (2013.01)
USPC .......................................................... 554/169

(58) Field of Classification Search
CPC .......... C07C 67/02; C07C 67/03; C07C 69/52
USPC ......................................................... 554/169
See application file for complete search history.

(56) References Cited

U.S. PATENT DOCUMENTS

| | | | |
|---|---|---|---|
| 5,399,731 A | 3/1995 | Wimmer | |
| 5,514,820 A | 5/1996 | Assmann et al. | |
| 5,520,708 A * | 5/1996 | Johnson et al. | ................. 44/388 |
| 6,262,285 B1 | 7/2001 | McDonald | |
| 6,489,496 B2 | 12/2002 | Barnhorst et al. | |
| 6,960,672 B2 * | 11/2005 | Nakayama et al. | ........... 554/169 |
| 2007/0175092 A1 | 8/2007 | Ames | |
| 2007/0196250 A1* | 8/2007 | Leveson et al. | ................ 422/187 |

OTHER PUBLICATIONS

Dunn, R. et al., Oxidative Stability of Biodiesel in blends with Jet Fuel by Analysis of Oil Stability Index, 2003, JAOCS, vol. 80, No. 10, pp. 1047-1048 (2 pages).*
Gerpen et al., Biodiesel Production Technology, 2004, National Renewable Energy Laboratory, NREL/SR-510-36244, 110 pages.*
Peterson et al., Rapseed Oil Transesterificatin by Heterogeneous Catalysis, 1984, JAOCS, vol. 61, No. 10 pp. 1593-1597 (5 pages).*
International Search Report from PCT/US2008/074927.

* cited by examiner

*Primary Examiner* — Yate K Cutliff
(74) *Attorney, Agent, or Firm* — Stoel Rives LLP (57) ABSTRACT

Alkyl esters boiling largely within the specification range for jet fuel may be made from triglycerides without a water-washing step, by centrifugation in a timely manner and at a sufficiently high time/G-force/distance product so as to bring about separation of a transitory second phase containing the residual catalyst. The esters or fractions thereof may be combined with jet or diesel fuels to lower the freezing and cloud points respectively.

11 Claims, 3 Drawing Sheets

METHOD FOR PRODUCTION OF BIOFUEL

RELATED APPLICATION

This application claims the benefit of and priority to U.S. Provisional Application Ser. No. 60/968,855, filed Aug. 29, 2007, the contents of which are incorporated by reference herein in its entirety.

BACKGROUND

The need for renewable energy sources includes the need to improve the fuel burned by jet engines. It would be advantageous to have a high-volume continuous-flow manufacturing process appropriate to the high-volume needs of this market, which could produce material within the boiling range of jet fuel. As is known to those skilled in the art, utilizing a water-washing process produces emulsions that are time-consuming and troublesome to break. The residual water itself must be removed to minimize not only corrosion and growth of harmful organisms, but to eliminate the possible formation of ice crystals in chilled fuel, it is desirable to manufacture such fuel without any process contact whatsoever with water.

According to statements in U.S. Pat. No. 6,015,440 to Noureddini, biodiesel was used as a fuel in South Africa before World War II. Although oils such as peanut oil could be used as diesel fuel, it can be assumed that at least some of the diesel fuel was made using transesterification of glycerides, which art goes back to the early days of soap-making. The transesterification of glycerides has been the subject of many patents. Early patents such as U.S. Pat. Nos. 2,271,619 and 2,360,844 to Bradshaw, et al., U.S. Pat. Nos. 2,383,580 and 2,383,581 to Arrowsmith, et al., Re22751 to Trent, U.S. Pat. No. 2,383,614 to Percy, U.S. Pat. No. 2,494,366 to Sprules, et al. and U.S. Pat. No. 4,371,470 to Matsukura were concerned with making esters as a means of making pure fatty acids for making soap. Other early patents such as U.S. Pat. No. 2,290,609 to Goss, et al., U.S. Pat. No. 2,634,279 to Kuhrt, U.S. Pat. No. 2,875,221 to Birnbaum and U.S. Pat. No. 3,083,216 to Alsop, et al. were concerned with making mono and diesters of glycerin.

There have been many processes developed for making biodiesel from glycerides. This disclosure will focus on those processes using a basic catalyst. It will also focus on continuous processes, although batch-reaction, batch-separation, batch-washing and batch-polishing processes may be incorporated into an otherwise continuous process, or large reservoirs may be continuously fed and drained, and the whole process called "continuous," as the biodiesel art is practiced. Strictly speaking, a continuous process has a continuous-flow everywhere, whether laminar or turbulent. It may be likened to a pipeline carrying a flowing liquid. A typical continuous process might be that described by Noureddini in U.S. Pat. No. 6,174,501. Triglyceride, methanol and catalyst are fed into a heated, stirred reactor. The upper layer is then fed into a separator. The upper layer is then passed through a deionization ("polishing") unit to become biodiesel product. This disclosure, however, takes a portion of mono and diglycerides for the purpose of making lower alkyl ethers of the mono and diglycerides and the glycerin itself. Thus, it does not seek completeness of reaction or purity of ester product for it teaches reduction of cloud point by the production of what might be described as a racemic mixture, or a rafinate including ethers.

Many patents have been issued for the form of the reactor in which the chemical reaction takes place. The triglyceride and methanol are not seen to be miscible beyond a limited degree of solubility, and patents such as Boocock in U.S. Pat. No. 6,624,399 teach the addition of co-solvents such as cyclic ethers to give a homogenous solution. Several patents suggest reactors with enhanced stirring. Assmann, et al. in U.S. Pat. No. 5,514,820 teaches having a Reynolds Number in excess of 2,300. Hooker in U.S. Patent Application Number 2005/0027137 teaches ultrasonics to facilitate the reaction.

There is a large amount of art dealing with handling of the products of such a reaction. It is concerned with gross separation of reaction byproducts and fine separation of small amounts of unwanted material, and is done by chemical means, physical means or a combination.

The fatty acid alkyl ester is lighter than the glycerin phase (unless a very large alcohol excess is used, e.g. 20:1), and will separate by gravity. Wimmner in U.S. Pat. No. 5,399,731 claimed that the addition of 0.3% to 3.0% water would facilitate the separation. In contrast, McDonald in U.S. Pat. No. 6,262,285 claims without examples that by eliminating all water and using a continuous decantation that the separation can be done very effectively. McDonald removes all water with Molecular Sieves, one type of sorbent. There is no evidence presented that the procedure is effective as claimed.

The use of a centrifuge to separate two phases of differing density is, of course, very old technology as demonstrated by the cream separators of the 1800s. Many patents mention, in passing, that a centrifuge could be employed in biodiesel production. For example, see Assmann in U.S. Pat. No. 5,514,820 col. 2 line 7 and line 13, Granberg, et al. in U.S. Pat. No. 5,648,483 col. 7 line 51, Matsukura, et al. in U.S. Pat. No. 4,371,470 col. 3 line 18 and in U.S. Pat. No. 4,668,439 col. 6 line 25, Hayafuji, et al. in U.S. Pat. No. 5,972,057 col. 15 line 38 and Noureddini in U.S. Pat. No. 6,174,501 col. 10 line 59. In Barnhorst, et al. U.S. Pat. No. 6,489,496, the essential claim was for the use of a centrifuge.

McDonald in U.S. Pat. No. 6,262,285 claimed that separation by decantation gave an acceptable product.

There is a consensus among those skilled in the art that traces of impurities can be very serious, in addition to not meeting current U.S. and European biodiesel standards. There are several ways of removing impurities, wherein the biodiesel is first water-washed and then dried. Three examples of water-washing are Tanaka, et al. in U.S. Pat. No. 4,303,590, Boocock in U.S. Pat. No. 6,624,399 and Felly in U.S. Patent Application Number 2006/0224005. Connemann, et al. in U.S. Pat. No. 5,354,878 proposes the use of an aqueous pH 8 to 10 buffer to wash the biodiesel. In contrast, Wimner in U.S. Pat. No. 5,434,279 washes with dilute acid such as citric acid. Bam, et al. in U.S. Pat. No. 5,424,467 proposes the washing to be with glycerin. Hayafuji in U.S. Pat. No. 5,972,057 proposes the use of a sorbent such as acid clay. Bertram, et al. in U.S. Patent Application Number 2005/0081536 proposes the use of adsorbent such as magnesium silicate. Noureddini in U.S. Pat. No. 6,174,501 uses an ion-exchange resin to remove the impurities.

DISCUSSION

The presence of any significant amount of particular mono- and diglycerides is due at least in part to insufficient reaction time/temperature/catalyst concentration. By means known to those skilled in the art, one may achieve an essentially complete reaction resulting in negligible amounts of mono and diglycerides. The following discussion is therefore not greatly focused on the removal of those particular impurities, although such removal may be accommodated incidentally.

The removal of undesirable matter from a biodiesel stream is known to be accomplished by washing or by sorbents.

Those skilled in the art know that washing is generally done with water or glycerin, although any liquid which does not dissolve the product in appreciable quantity could, in principle, be used. Emulsions commonly form with water-washing and may form with other washing liquids. These are believed to form due to the presence of residual phyto-sterols, phospholipids and biological byproducts which act as emulsifying surfactants. In the course of making biodiesel batches from both Palm Kernel oil and Canola oil (rape seed oil), it was observed when experimenting with water-washing that the Canola biodiesel formed stronger emulsions that took much more effort to break and finally clean up, compared to the Palm Kernel oil. One may reduce the occurrence of emulsions by very slow water-washing, as with water droplets falling through a rising stream of alkyl ester oil. Very slow water-washing is not compatible with a high-volume continuous-flow process design. Washing may also be performed in the inverse manner wherein a suitable solvent dissolves not the impurities but rather the desired ester product, and separates said product from matter not desired in the final product. Exemplary of inverse washing in the prior art is Peter, et al., U.S. Pat. No. 6,211,390.

Sorbents include those rather passive in their action, such as Magnesol, for example, a magnesium silicate (talc) material thought of as inert. Sorbents include molecular sieves. Sorbents may also be more active ones, such as a dehydrated acid-form ion-exchange resin. Such a material can hold, by hydration, hydroxyl functional materials such as water, alcohol, glycerin, monoglycerides and diglycerides, and even fatty acids. By ion-exchange, an alkali-metal catalyst may also be sequestered. There may be other possible kinds of sorbents but they all have the disadvantages, whether in bed form or suspension, of being a solid matter that may become waste after its removal from the process stream, or from the packed chamber through which the process stream is filtered. While such a process is apparently in principle compatible with a continuous-flow manufacturing process, it is not the ideal structure of such a process. In an ideal continuous-flow manufacturing process, everywhere in the process materials are flowing through the various mixing and treatment and reaction zones. Where such a continuous-flow process can be realized, it will produce a product of the most consistent properties.

Jet engines require fuel which breaks into very small droplets having a large combustible surface area when injected at high pressure through an orifice, becoming atomized in the combustion chamber of an engine. Specifications have been written to define petroleum products with physical and chemical properties in the range that current engines are designed to accommodate. It is believed that the upper and lower-boiling range specifications derive from an early effort to control viscosity so as to obtain a certain degree of atomization behavior during injection. There are two natural triglycerides (Cocoanut oil and Palm Kernel oil) commonly available that have fatty acids largely in the C8-C14 range. These fatty acids, if converted to their methyl ester form, viz. fatty acid methyl esters (FAME), would be expected, based on their molecular conformations and molecular weights, to boil within the boiling range specification for Jet fuel.

It is well-known to those skilled in the art that triglycerides may be fed directly into a thermal cracking process, and the raffinate stream fractionated and/or isomerized as necessary to produce material that, when fractionally distilled, gives some portion of material that boils within the range of Jet fuel, although lighter and heavier fractions suitable for heating oil and for gasoline may also be obtained. It is a disadvantage that the manufacturing plant for such material may cost in excess of a hundred million dollars, and small-scale plants are not economically possible. It is therefore desirable to have a manufacturing process whose production plant costs far less, and which may be established on both large and small scales as the local needs vary. Esterification of natural triglycerides with methanol, ethanol, etc. is a process that is feasible on very small, intermediate and large scales.

The low molecular weight alcohol commonly used is methanol. Methanol is currently produced from natural gas, by a controlled partial combustion, converting it to Synthesis Gas, a mixture of carbon monoxide and hydrogen, and then converting that in large part to methanol. The facility for doing this is only practical to construct on a large scale. There are two methods of overcoming this barrier to the basic goal of the instant patent application and both are, per se, in the public domain. They are summarized here for conceptual completeness of the instant disclosure. One method is to use an alcohol, particularly ethanol, which can be obtained from renewable sources by means known to those skilled in the art, and indeed is currently being produced in high volume by such means as enzymatic action or fermentation of corn mash. The second means is to make methanol from renewable energy sources, such as by destructive distillation of cellulosic material. One might recall that methanol, also known as methyl alcohol, was originally called wood alcohol, so named for its early method of manufacture.

It is also to be noted that Jet engine fuel, whether made from non-renewable or renewable sources, may be burned in turbine engines that are, in one application, coupled to electrical generators. If made from renewable resources, the fuel production will not contribute significantly to global warning as it can be made entirely from plants which draw their carbon from the carbon dioxide in the atmosphere. Therefore, one goal of this disclosure is to describe the production of such fuel on an industrial scale by efficient continuous industrial processes, regardless of the source of the alcohol component of the ester structure.

FURTHER DISCUSSION

We have discovered that in the minutes and hours after certain transesterification reactions, when the reaction mixture is allowed to stand undisturbed, the normally cloudy ester phase actually contains a suspended phase, which at first settles out to a degree but may redissolve after some days. This material is alkaline, and settles under the influence of gravity. It follows that its separation may be accelerated by a centrifuge such as is used to separate liquids (or liquids with suspended solids) of differing densities. This allows an improved efficiency in the manufacture of esters wherein a degree of purity is desired, over that obtained by a gross separation of glycerin from ester by conventional storage-tank settling or cyclonic separation. It also offers a simplified manufacturing process by the elimination of a water-washing step such as is commonly used to remove a homogenous catalyst.

An improved manufacturing process incorporating this process will now be described, for the particular but non-limiting case of production of a methyl ester of a triglyceride, such as may be obtained from plant sources. Of course, animal, algal or any other source of glyceride may be used with this technology, and other alcoholic esters.

Triglycerides such as may be obtained from animal or vegetable sources are purified by appropriate means to yield a triglyceride substantially free of fatty acids, water and such phyto-sterol, phospholipids, antioxidants, and other trace ingredients as may be troublesome to the subsequent process or as may have incidental commercial value. Beside such phyto-sterol recovery as may be appropriate to the particular oil, traces particularly of water and free fatty acids are removed by low pressure distillation in a wiped-film evaporator, falling-film evaporator or similar. An inert atmosphere is flushed through the system to aid the removal of residual water and free fatty acid vapor, as well as to prevent oxidation during the entire process. The purified triglyceride is combined with an alcoholic solution of an alkaline catalyst. Noteworthy examples of a suitable alkaline catalyst are sodium methoxide, potassium hydroxide and the like, although it is understood that any alkaline catalyst known to those skilled in the art may be used in the process.

The alcoholic solution of catalyst is combined with the triglyceride in a mixer of intimacy such as an emulsion mill. These are commonly used in the asphalt industry for making water based asphalt emulsions. It is to be understood that any mixer may be used, with the initial reaction rate limited by the contact area of liquids that may at first be of limited mutual solubility and thus a two-phase system. While prior art uses batch processes and stirring, and settling tanks, and such may still be used, the preferred implementation of this technology maintains a continuous-flow, in that the output from the mill proceeds through a plug-flow process loop to give residence time sufficient for the transesterification reaction to run essentially to completion. Residence time at a temperature may be found experimentally for the particular oil and catalyst and alcohol concentration, by means commonly known to those skilled in the art, and scaled to other temperatures to obtain desired reaction times. The time-temperature product will vary with catalyst type, concentration and intimacy of mixing. For example, May in the *Journal of Oil Palm Research* Vol. 16, No. 2, December 2004, pp. 1-14 found that increasing the temperature decreased the time required for completion by factors ranging from 4 to 2 for each ten-centigrade degree increase. So, two hours at 70 C may give the equivalent result as one hour at 80 C, a quarter-hour at 10° C., and so forth. The process loop may be the length of a single tube or many smaller parallel tubes such as is found in large heat-exchangers. The pipe or tube may contain static mixing elements or such packing material as may be appropriate to maintain sufficiently mixed state for the reactants during their residence time in the reactor. A temperature appropriate to the residence time is maintained from the mixer to the end of the process loop.

With subsequent cooling and/or cessation of mixing, a glycerin phase separates. The excess alcohol is partitioned between the ester phase and the glycerin phase depending on the relative solubility of the alcohol in the glycerin and in the particular ester or ester mixture formed. Depending on how much of an excess of alcohol is used, and the density difference between the alcohol and ester, a less dense glycerin/alcohol phase will separate and float above a more dense ester/alcohol phase or the less dense ester/alcohol phase will float above a more dense glycerin/alcohol phase. In these examples and the subsequent discussion it is assumed that an excess of methanol, about one to two moles more than that needed for a stoichiometric reaction, is used, and thus a more dense glycerin/alcohol phase forms and settles to the bottom, but this choice is not intended to limit the scope of the process.

The major part of the glycerin/alcohol phase may be easily separated on a continuous-flow basis by gravity, in settling tanks of various batch or quasi-continuous arrangement, or by simple continuous-flow means such as a cyclonic separator. Cyclones are well known, not merely for separating fluids of different densities, but for separating particulates from gas streams, such as particulate ash from a combustion process or sawdust from air flushed through a wood-products-manufacturing operation.

At this point it would not be obvious to employ a second centrifugal separation process, nor one of high-G magnitude and duration as is described in subsequent portions of this patent, and yet this step will produce a surprising degree of separation of materials that are at this point insoluble at least on a transient basis. The rationale of this centrifugal step will now be described in more detail.

From the experiments described in the Examples, we see that there is visible material that settles with time, and the visible settling matter has some alkaline material in varying concentration. By accelerating this process with a centrifuge of performance appropriate to the observed settling rate of the unwanted matter, a vastly improved biodiesel production process will result.

The settling rate of a spherical (we assume the particles are spherical to simplify calculations because their exact shape is unknown and likely varies irregularly; the spherical assumption has been found to give adequate practical results in physics generally) particle in a fluid (air or gas) having a characteristic viscosity, varies with the particle radius, according to the laws of physics. Formulas that are known to those skilled in the art include the following. From the website, http://www.sciencebyjones.com/Viscosity.htm: Theory: An object falling through a viscous medium will reach a terminal velocity [constant velocity, no acceleration] when the sum of the buoyant force and the viscous force equals the force of gravity. For a sphere of radius (r) in a fluid of density ($\rho$), $$F_{buoyancy} + F_{viscosity} = F_{gravity}$$

$$F_{buoyancy} = \tfrac{4}{3}\pi r^3 \rho g \quad F_{viscosity} = 6\pi \eta r v_t \quad F_{gravity} = mg$$

where $v_t$ is the terminal velocity and $\eta$ is the viscosity. g is given as 980.7 cm/s$^2$ Alternate Formula:

$$\text{Viscosity}(\eta) = 2bga^2/9v$$

where b=difference in density between the sphere and the liquid, g=acceleration of gravity, a=radius of sphere, and v=velocity (d/t))

And so, by solving for v, the terminal velocity, we see that we have an entire spectrum of velocities, varying directly as the square of the particle radius, just to the extent that we have a spectrum of effective radii of the suspended particles.

From the observational data of Example Two below, it is elementary to calculate a range of G-forces needed in an industrial centrifuge to separate the cloudy matter containing residual base and residual glycerin and glycerides from the methyl ester. Let us take from observation a settling distance of 0.9 mm/hr at one G as a starting point for a centrifuge specification. If the average radial annular distance within the centrifuge at which the annulus of liquid spins is 90 mm, then clearly at one G, 100 hours is required. At 100 Gs, 1 hour would be required, and at 6000 Gs, a residence time within the centrifuge of one minute would be required to separate the suspended alkaline matter. The motor required to drive this centrifuge would have to have enough horsepower to accelerate the desired liquid throughput up to a rotational velocity sufficient to give about 6000 Gs over the 90 mm radial distance. Naturally, a turbine at the exit end could recover a significant fraction of the rotational energy by decelerating the rotating liquid and feeding that energy back to the input shaft. Accordingly, an industrial centrifuge may be designed and applied to this task by means known to those skilled in the arts.

Naturally, if 6000 Gs for one minute is a design specification, one may use 600 Gs for ten minutes, or any time-force product as gives the equivalent result. Since the size of precipitated catalyst particles and/or glycerin/glyceride emulsion droplets will vary within broad ranges depending on the type of oil run and the natural tendency of the oil with its natural emulsifiers such as lethcin, to give emulsions or suspensions, that tendency also dependent on the particular alcohol used, it follows that required centrifuge residence times will vary accordingly. The general range of centrifuge requirements may be in any case obtained by simple observations as described above.

According to the above examples, a high degree of "polishing" of the finished ester will be obtained without resorting to water-washing and the attendant inconvenience of breaking the ubiquitous emulsions, removing the residual water, or the expense of "polishing" with an ion-exchange resin or other sorbent.

Following this centrifugal step, the process flow may offer an alcohol-stripping step to remove the light ends, consisting essentially of the excess alcohol that may remain dissolved in the ester. It is desirable to do this so that a final distillation step, if employed, is not burdened with the additional vapor-load of a relatively low-boiling material that will be recovered and returned to the process stream. Accordingly, one may employ such as a wiped-film evaporator or falling-film evaporator or similar, which may operate at the temperature of the incoming process stream or may be heated. The vapor taken off may be at reduced pressure or a pressure higher than atmospheric, although atmospheric pressure is preferred, to simplify the design. A condenser may be used to return the vapor to a liquid state, if that is more desirable for reutilization within the overall process. An inert-gas flush is highly desirable, to efficiently carry off essentially all of the alcohol, because its presence in the final product is not desired. The European biodiesel standard (EN14214) limits methanol to 0.2%. The American ASTM D6751 requires a flash point, closed cup, of 130 C which requires a lower methanol content, in the range of hundreds of parts per million.

The output of such a light-ends-stripper may then be conveyed to a distillation column, for final purification of the process stream according to its end use. Light distillate, such as boils in the approximate range of 100-150 C at about a tenth of an atmosphere, may fall within the range of Jet fuel or #2 Diesel. Higher-boiling materials may fall within the range of heavier fuel materials, such as heating oil, and a still-bottoms stream may be used for applications that do not require particular conformance to particular fuel standards, such as burning within the manufacturing facility for process heat. Various steps require heating, and there is an economic tradeoff between the quality of insulating structures, their cost, and the efficiency of heat-exchangers. Thus, some heat is inevitably lost as a practical compromise to manufacturability and economic viability. This heat can be supplied by burning the less desirable products of the manufacturing process. Since these materials are derived from atmospheric carbon dioxide by photosynthesis, it follows that their combustion and reduction to carbon dioxide and recovery of the stored solar energy originally captured by the plants, the return of such carbon dioxide to the atmosphere essentially does not produce a net effect upon the planetary ecosystem.

DESCRIPTION OF DRAWINGS DEPICTING A PREFERRED EMBODIMENT

Figure 1:
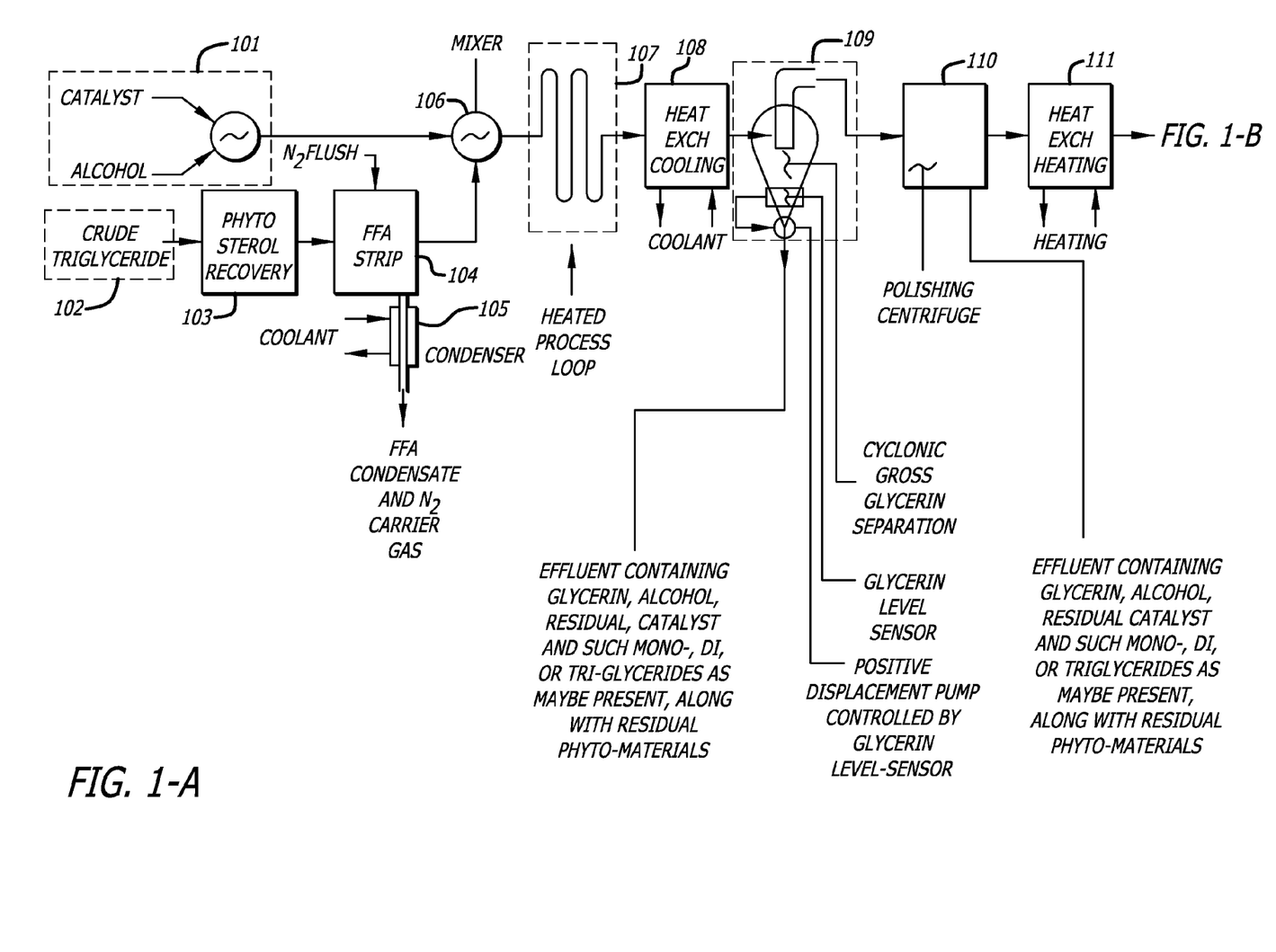
FIG. 1A is a schematic representation of initial steps of a method for the production of a biofuel.
FIG. 1B is a schematic representation of further steps of a method for the production of a biofuel.

The figures in this disclosure depict a preferred embodiment of the system. Describing FIGS. 1-A and 1-B, element 101 is a source of a catalyst, combined with an alcohol as an example. The catalyst, alcohol and purified triglyceride may of course be all combined in the mixer 106 or just prior to entering the mixer; for clarity in the drawing, the catalyst and alcohol are shown as being precombined. These materials are managed by strict process controls so that a specific ratio of the components is maintained. The ratios are based on the triglyceride content of the feed stock. The triglyceride content is determined by known techniques such as testing in the tank or by in-line sampling. This information is used to manage the ratios of the raw materials. The process controls determine the proper amount of alcohol and catalyst based on the feed stock triglyceride content.

Element 102 is a source of a triglyceride such as palm oil, palm kernel oil or rape seed oil. This oil has had substantially all of the water removed prior to entry of the oil into this process. Water is not added during any subsequent step during the process described herein.

Element 103 is such recovery as may be appropriate to the particular triglyceride feedstock. Examples of recovered compounds are phytosterol, phospholipid and other trace compounds as may be of value or troublesome to the subsequent esterification process.

Element 104 is a vacuum distillation process to pretreat the crude triglyceride, typically a wiped-film evaporator, falling-film evaporator or similar, at an exemplary temperature such as 100-150 C and an exemplary pressure on the order of a tenth of an atmosphere, typically inert-gas flushed, such as to remove particularly any water or free fatty acids which can subsequently consume transesterification catalyst and form troublesome soaps.

Element 105 is a condenser such as may be appropriate to the vapor passing out of 104.

Element 106 is a mixer of physical intimacy (e.g. high shear), normally producing a heating of the process stream, which, in this embodiment, combines the triglyceride flow and the alcohol/catalyst flow. An additional heater may be used, for example, in the stream between elements 104 and 106. The combined mixture is raised to a process temperature of approximately 140 C to 160 C and the pressure is maintained high enough so as to prevent the liquids from turning into vapor, approximately 10 psi to 30 psi. Thereby, the reaction occurs quickly, for example, in less than a minute. Of course, the temperature and pressure may be adjusted depending on the parameters in which the system is operating. Typically, in the prior art processes the operating temperature is 60 C to 65 C and the pressure is atmospheric.

Element 107 is a process loop of suitable configuration, maintained at an intended process temperature, providing a plug-flow environment for the reactants in transit from an entry port to an exit port, such that materials entering the element are held at an intended temperature for an intended time and then conveyed to the next process element. In its simplest form, this element might be a length of tubing or pipe, preferably with suitable packing material, to maintain a plug-flow environment for the material in transit. "Plug-flow" means that a unit quantity of material entering, nominally exits as such a unit quantity.

Element 108 is a heat exchanger that changes the reactant mixture from its reacting temperature in the prior element to a temperature suitable for the intended performance of the next process element.

Element 109 is a glycerin-ester separation element. One suitable element is a cyclone, wherein the mixture of glycerin and ester is injected near the circumference of a circular element, and centrifugal force causes the more dense phase to migrate to the outer circumference and the less dense phase to migrate in the direction of the axis. In the case of a more dense glycerin/alcohol phase and a less dense ester/alcohol phase, a cyclone is shown in the drawing, and a vertical gravitational field (not shown in the drawing) causes the more dense glycerin/alcohol phase to migrate down and be drawn into a smaller space by the conical shape of the cyclonic separator, as such devices are called. Shown in the drawing but not described as separate elements are, at the bottom of the cyclone, a glycerin level sensor controlling a positive-displacement pump that removes glycerin as it accumulates but does not remove the lighter ester/alcohol phase, such ancillary elements being well known to those skilled in the art.

Element 110 is a centrifuge such as is described in the specification, second example and claims.

Element 111 is a heat exchanger that changes the process stream to a temperature suitable for the intended performance of the next process element.

Element 112 is a wiped-film evaporator, falling-film evaporator or other comparable element that strips the much more volatile residual alcohol from the much less volatile ester process stream. It is preferably inert-gas flushed, to aid in the removal of residual alcohol vapor that would put an undesirable vapor burden on element 114, a distillation step, whose top distillate takeoff is preferably the desired product, in the absence of lower-boiling material.

Element 113 is a vapor condenser as needed for condensing the vapor of the low-boiling material removed from the process stream, such that its liquid condensate may be utilized in the overall process, should that be preferable.

Element 114 is a distillation element of sufficient theoretical plates so as to separate the process stream into two or more process streams having generally different boiling ranges, such as may be desirable for different further uses of said process streams. In the figure, one process stream is the lowest-boiling stream, which is shown being taken off as vapor at the top of the distillation column; another process stream, for example, is shown being taken off part way down the column, at a higher temperature, it being conventional to represent higher temperatures near the bottom of the column and lower temperatures at the top, since this corresponds to how the ordinary distillation columns operate, where the external gravitational field draws more dense liquids to the bottom and less dense vapors to the top. A third takeoff is shown at the bottom, where materials may boil at a high temperature so that it is preferable to remove them as a liquid stripped of lower-boiling materials. An optional level sensor and liquid sensor is shown and may be employed should it be desirable. The process depicted in element 114 is intended to include a continuous fractional distillation process. During the distillation of the FAME, various boiling point fractions are separated to remove undesirable components from the FAME such as excess methanol, mono and diglycerides and any excess glycerol. Finally, the FAME is broken into individual boiling point fractions which are each useful for different forms of fuel, such as jet fuel and diesel fuel. Some of the fractions can be used as cloud point or freeze point suppressants. The lighter fractions (e.g. the top 20%) are suitable for blending with jet fuel to lower the freeze point. The remaining fractions are suitable for blending with diesel fuel to lower the cloud point. Of course, the heavier fractions can be used as diesel fuel itself, in addition to being used as a blending component. In fact, any or all of the fractions may be blended with diesel fuel, or the entire output may be used as diesel fuel under the proper conditions. The jet and diesel fuels referred to herein may be entirely petroleum based, biofuels or a blend.

Element 115 is a vapor condenser, whose output is a condensate process stream, boiling within the specification range of Jet fuel.

Element 116 is a vapor condenser, whose output is a condensate process stream, boiling at a higher temperature range than that of the condensate of element 115.

Element 117 is a higher-boiling distillate, the condensate out of element 116. Where the condensate of 116 is intended to be distillate boiling in the range of Jet fuel, such being a major distillation fraction of the methyl esters of Palm or Cocoanut oils, there is a higher-boiling fraction of such triglyceride esters which is suitable for #2 diesel or higher-boiling applications. Therefore this distillate is shown to represent recovery of fractions for other uses than Jet fuel.

Figure 2:
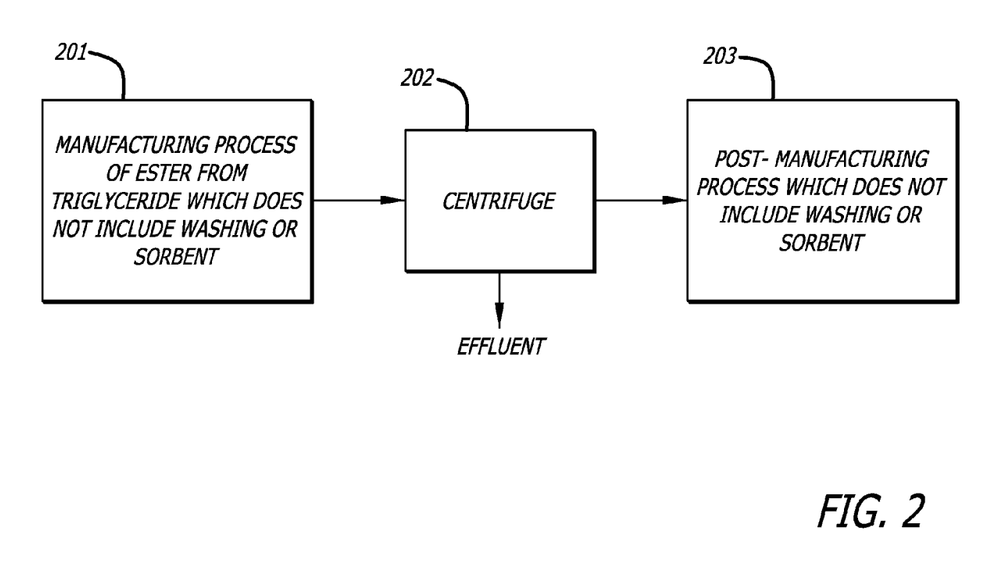
FIG. 2 is an overview of the method of FIGS. 1A and 1B.

Describing FIG. 2, element 201 is any manufacturing process of an alkyl ester from a triglyceride stream, not including a washing step or a sorbent step.

Element 202 is a centrifuge whose G-force/residence time product is comparable to or more than the observed settling rate of suspended matter as described in the examples: nominally {6000 G×1 minute for 90 mm radial distance}, and which has an effluent stream of more dense matter separated from the process stream exiting 201.

Element 203 is any post-centrifuge process which does not include a washing step or a sorbent step.

DESCRIPTION OF A PREFERRED EMBODIMENT OF THE PROCESS

Triglycerides such as might be obtained from animal or vegetable sources are purified by appropriate means to yield a triglyceride substantially free of fatty acids, water and such phyto-sterols antioxidants, and other trace ingredients as may have incidental commercial value. Beside such phyto-sterol recovery as may be appropriate to the particular oil, traces particularly of water and free fatty acids are removed preferably by low-pressure distillation in a wiped-film evaporator, falling-film evaporator or similar element. An inert atmosphere is flushed through the system to aid the removal of residual water and free fatty acid vapor, as well as to prevent oxidation during the entire process. The purified triglyceride is combined with an alcoholic solution of an alkaline catalyst. Sodium methoxide is readily available, and is preferred if the catalyst is recycled within the process loop. Sodium ethoxide is preferred if one is making the ethyl ester rather than the methyl ester. Similarly, potassium methoxide or ethoxide may be used, and potassium is preferred over sodium where the catalyst or substantial part thereof appears in a waste stream of the process, for potassium salts have been used as fertilizer and thus would not be unusable waste.

An alcoholic solution of catalyst and a triglyceride are measured in proportions such that for every mole of fatty acid ester in the triglyceride, there are enough alcohol moles, preferably an excess, to bring the reaction to a desired degree of completion. It would be unusual to use as little as a ten percent excess. The reaction is promoted to a high degree of completion if there is about an equimolar excess. This also reduces the viscosity of the glycerin product of the reaction, as the alcohol dissolved in the glycerin reduces the glycerin-phase viscosity and facilitates its separation. One may use a two-fold or three-fold molar excess, and about an one-to-two fold molar excess over stoichiometric requirements is preferable. If one elects to use a high-molar excess, such as about fifteen, the glycerin-phase may become less dense than the alkyl-ester phase, and float on top instead of sink beneath. This may be desirable in some implementations of this technology.

The alcoholic solution of catalyst is combined with the triglyceride in a mixer of intimacy. An emulsion mill is preferable for it is ready availability. It is to be understood that any mixer may be used, with the initial reaction rate limited by the contact area of liquids that may at first be of limited mutual solubility and thus a two-phase system. The preferred implementation of this technology maintains a continuous-flow, in that the output from the mill proceeds through a process loop to give residence time sufficient for the transesterification reaction to take place. The process loop may be a length of single tube or many smaller parallel tubes such as are found in large heat-exchangers. The pipe or tube may contain static mixing elements or such packing material as may be appropriate to maintain a sufficiently mixed state for the reactants during their residence time in the reactor. A temperature appropriate to the residence time is maintained from the mixer to the end of the process loop.

With subsequent cooling and/or cessation of mixing, and a complete or nearly complete reaction, a glycerin/alcohol phase separates. The excess alcohol partitions between the ester phase and the glycerin phase depending on the relative solubility of the alcohol in the glycerin and in the particular ester or ester mixture formed. Depending on how much alcohol is used, and the density difference between the alcohol and ester, a less dense ester/alcohol phase will float above a more dense glycerin/alcohol phase or a less dense glycerin/alcohol phase will float above a more dense ester/alcohol phase. In these examples and the subsequent discussion it is assumed that an excess of methanol, one to two moles more than that needed for a stoichiometric reaction, is used, and thus a more dense glycerin/alcohol phase forms and settles to the bottom, but this choice is not intended to limit the scope of the process.

The major part of the glycerin/alcohol phase may be easily separated on a continuous-flow basis by gravity, in settling tanks of various batch or quasi-continuous arrangement, or by simple continuous-flow means such as a cyclonic separator.

There is no prior water-washing step or sorbent step.

The next step is a high-G-force separation step. Let us take a settling distance of 0.9 mm/hr at one G as a starting point for a centrifuge performance specification, based on an observation of settling rate of transitory suspended matter. If the average radial distance at which the annulus of liquid spins is 90 mm, then clearly at one G, 100 hours is required, at 100 Gs, 1 hour would be required, and at 6000 Gs, a residence time within the centrifuge of one minute has been calculated as being required to separate the suspended alkaline matter.

Naturally, if 6000 Gs for one minute is a design specification, one may use any time-force product as gives the equivalent result. Since the size of precipitated catalyst particles and/or glycerin/glyceride emulsion droplets will vary within broad ranges depending on the type of oil run or even the particular alcohol, and any tendency of natural phytosterols, phospholipids, etc., to give suspensions, it follows that required centrifuge residence times will vary accordingly. The general range of centrifuge requirements may be in any case obtained by the simple observations as described above.

There is no subsequent water-washing step or sorbent step.

Following this centrifugal step, the process flow may include an alcohol-stripping step to remove the light ends, consisting essentially of the excess alcohol that may remain dissolved in the ester. It is desirable to do this so that a final distillation step, if employed, is not burdened with the additional vapor-load of a relatively low-boiling material that will be recovered and returned to the process stream. An inert-gas flush is highly desirable, to efficiently carry off essentially all of the low-boiling components and to prevent oxidation. The stripped output of such a light-ends-stripper may then be conveyed to a distillation column, for final purification of the process stream according to its end use.

EXAMPLE #1

1000 grams canola oil, 240 grams methanol, and thirty grams of a thirty percent solution of sodium methoxide in methanol was stirred in a 4 liter Erlenmeyer flask with a five-inch Teflon-coated stirring magnet, said flask fitted with a reflux condenser, on a hot plate for two hours at a temperature of about 65 C. The reaction was deemed completed at that time and the mixture was then allowed to cool to about 50 C and then decanted into a separatory funnel. The glycerin phase was seen to be separated a few minutes later, and 1000 ml of the cloudy upper ester phase was placed in a graduated cylinder and allowed to stand at room temperature for about thirty hours. A clear region at the top was observed to form, about a centimeter in height. Samples of four cc in volume were withdrawn from various depths, by means of a syringe and a long needle. The samples were each washed once with 16 cc of deionized water, allowed to stand a few hours, and the bottom six cc of water withdrawn and placed in a test tube. These were photographed, and it is clear from the differences in cloudiness that different compositions exist at different depths. The pH of each layer was measured by means of a pH meter using a solid-state FET electrode, and the measurements from the top down were: from the top 20 mL, pH=7.5-7.9; from the 750 mL level [250 down], pH=7.8-7.9; from the 500 mL level, pH=8.3-8.4; from the 250 mL level, pH=8.0-8.3; from a level about 20 mL above the thin layer of glycerin developing on the bottom, pH=8.2-8.3; and, for the sampled bottom glycerin layer itself, pH=11.2-11.3. The ranges of pH represent two successive measurements of the same material, reflecting some uncertainty in the measurements. Nonetheless, it is clear that there is a significant variation in pH that cannot be explained except by something settling at some rate.

It is clear that there is a gradient of concentration of suspended alkaline material, with the top layer being almost neutral and the base concentration increasing almost an order of magnitude as one nears the bottom, with the glycerin layer at the bottom being about 3.5 orders of magnitude higher base concentration than the top of the ester layer.

It is clear that if that material were centrifuged, the separation of upper matter from (at least temporarily) insoluble lower matter would happen quickly, and the upper ester layer would be purified.

An analysis by gas chromatograph showed the reaction to be essentially complete, and to contain a negligible amount of mono or diglyceride.

The conditions necessary to obtain a particular residence time can be calculate from experimental data. If one observed a reaction time of two hours at 65 C, one hour at 75 C and ½ hour at 85 C, one would extrapolate that this reaction would attain a similar degree of completeness in about 15 minutes at 95 C, about 8 minutes at 105 C, 4 minutes at 115 C, etc. To conduct this reaction on a continuous-flow basis, a process loop is chosen to provide the required residence time. After cooling and centrifugal separation of the glycerin/alcohol phase, a further centrifugal separation step removes he residual glycerin and catalyst, and the material may be methanol-stripped and distilled if desired.

EXAMPLE #2

1440 grams of Palm Kernel Oil was placed in a 4 liter flask with a stirring bar magnet, on a hot plate with a magnetic stirring motor. This was about two moles, the molecular weight being about 720. 18 moles of methanol, of molecular weight 30, or a total of 540 grams, was added, along with 34 grams of a thirty percent solution of sodium methoxide in methanol. The mixture was warmed with stirring and held in the temperature range of 60 to 70 C for two hours. It was then allowed to cool with stirring for about ½ hour, to a temperature of about 45 C, and poured into a four-liter separatory funnel. Within a few seconds a layer of glycerin formed at the bottom, and within another minute the "rag layer" at the interface had dissipated, leaving an almost mirror-clear interface. The glycerin was drained out the bottom, and about 1020 mL of the cloudy methyl ester layer was placed in a 1000 mL graduate, with a 4 mL sample taken to represent the average of suspended matter. Its pH was measured in the manner previously described and found to be 9.3-9.4. Upon another hour standing at room temperature, the ester had cooled further and the volume was close to 1000 mL.

The physical dimensions of the 1000 mL graduated cylinder were about 6 cm in inside diameter and the graduated portion 35 cm in length. Accordingly, by calculation, the 10 mL graduations were found to be spaced 0.35 cm apart.

In a period of about 1½ hours (at about 20 C) a well-defined clear layer about four cc in volume was observed to form at the top of the 1000 mL graduate of freshly-run palm kernel methyl ester. In about three hours a well-defined clear layer of about eight cc had formed at the top of the 1000 mL graduate. At this point four cc samples were withdrawn at various depths within the graduate. The pH measurements of water-extracts of these samples as a function of depth, starting at the top, were, from the top 20 mL, pH=9.2-9.4; from the 750 mL level [250 down], pH=8.3-8.5 [this measurement is suspect]; from the 500 mL level, pH=9.5-9.6; from the 250 mL level, pH=9.9-10.0; from a level about 20 mL above the thin layer of glycerin developing on the bottom, pH=9.5-9.8; and, for the sampled bottom glycerin layer itself, pH=11.6-11.7.

The remainder was allowed to stand overnight.

In a further eighteen hours a poorly-defined somewhat clearer layer of about 150 to 300 cc in volume was observed in the upper 150-300 cc of ester in the graduate. The clarity decreased downwards, with the lower third about as cloudy as when the graduate was initially filled, if not more so. This behavior is consistent with a distribution of sizes of particles of slightly higher density than the ester, slowly settling under the influence of a force of one gravity.

At twenty hours a second set of samples were taken from various depths, as previously described, and their pH measured in the aforesaid manner. From the top 20 mL, pH=9.3; from the 750 mL level [250 down], pH=9.6; from the 500 mL level, pH=9.6-9.7; from the 250 mL level, pH=9.7-9.8; from a level about 20 mL above the thin layer of glycerin developing on the bottom, pH=9.3-9.4; and, for the sampled bottom glycerin layer itself, pH=11.4-11.7.

The earliest settling observations were about 0.14 cm in 1½ hours, and about 0.28 cm in about three hours, both of which equate to about 0.09 cm/hour at one G. The later settling observation was about five to ten cm, roughly, in about 18 hours, or about 0.28-0.56 cm per hour at one G. It is likely that Brownian motion is competing with settling in the later measurement and blurring the effect. However, there may be a resolubilization phenomenon or some chemical reaction taking place, for in about 21 hours the entire graduate had become almost clear, with only the lower third slightly more hazy than the upper portion. The room temperature was not varying appreciably during this period, so temperature did not seem to be the cause. The clarity was not "crystal clear" as was the initial layer of ester in the first few hours, but was substantially more clear than the lower portion in the first few hours. By the next day the entire graduate had become pale yellow and crystal clear, except for the thin orangish glycerin layer at the bottom, about ten to twenty milliliters. This behavior is consistent with something redissolving, and thus it is highly likely that there are several things going on at once.

A third set of samples was taken in the previously described manner, about 70 hours after the initial reaction mixture was decanted. Their pH was measured in the aforesaid manner. From the top 20 mL, pH=9.4-9.6; from the 750 mL level [250 down], pH=9.5-9.7; from the 500 mL level, pH=9.4-9.8; from the 250 mL level, pH=9.6; from a level about 20 mL above the thin layer of glycerin developing on the bottom, pH=9.5-9.6; and, for the sampled bottom glycerin layer itself, pH=11.5-11.6.

It is to be noted that the water extractions and stirrings, and handlings of the pH samples must be kept covered to the best extent possible, for there is little total alkaline material present, and stirring uncovered can pick up enough carbon dioxide from the air to reduce or even neutralize the base, thus masking this effect. It is believed that this happened to some degree in the experimental process of the previous examples, although it was not realized until much later.

We took the palm kernel oil FAME of this example 2 and distilled it into various fractions. We then took the fraction that constituted the first 20% of the distillation and determined the freeze point of this fraction to be minus 16 C. We then blended this top 20% fraction with a petroleum aviation jet fuel having a minus 40 C freeze point in the ratio of 80% of the jet fuel and 20% of the top 20% fraction. An unexpected result occurred in that the freeze point of the mixture decreased to minus 56 C. Mixing with other percentages and ratios may yield advantageous results as well. Additionally, it is probable that mixing fractions lower than the top 20% fraction of the distillate will yield advantageous results, as by lowering the freeze point as well. Persons skilled in the art will be able to determine optimal mixtures of the fractions and the ratios. Similarly, combining all or a portion of the fractions of the material generated by our process with diesel fuel will lower the cloud point of diesel fuel.

Discussion

It is therefore an object of this process to produce a biofuel material by esterification of a triglyceride such as is produced by biological life and thus a renewable resource. It is a further object of this process to produce a biofuel product whose boiling range is within the boiling range specified for jet fuel. It is further object of this process to eliminate scientific and technological barriers to a continuous-flow manufacturing process. In all the prior art it is seen that there are certain common elements that make the overall process awkward and necessitate unusual solutions.

Heterogeneous catalyst technology is known in principle but the science is not well-enough developed that it can be applied on an industrial scale, thus homogenous catalysts are used, with their attendant problems of post-reaction removal, or extreme reaction conditions are used to bring about an esterification reaction without a catalyst. In either case there remain the problems of removal of unreacted starting materials, residual glycerin, catalyst residues, phyto-sterols and related contaminants normally found in oils produced by biological life, as barriers to the continuous-flow production of a high-quality esterified fatty-acid product.

The removal of residual alkali catalyst is particularly troublesome, and even some large-scale industrial production uses large settling tanks to allow the heavier glycerin phase to separate in its normally slow manner from the lighter oil-phase, because most of the alkali catalyst remains dissolved in the glycerin/alcohol phase, and most of that separates on standing. Only a small amount of alcohol dissolves in the oil-phase due to the preference of the alcohol to dissolve in the more polar glycerin phase. We believe the catalyst partitions accordingly, with most of the alkali hydroxide or alkoxide dissolving in the glycerin/alcohol phase and only a small amount dissolving in the alcohol/ester phase. Without wishing to be bound by this theory, it is believed that the glycerin precipitating out of solution at the end of the reaction brings about a transient condition wherein the residual catalyst exists in an emulsion phase with other materials in which it has some solubility. At this moment it can be centrifugally separated due to its higher density. With time, this transient emulsion phase dissolves in large part in the oil-phase, and accounts for the residual catalyst commonly found in many unwashed biodiesel products.

The transient existence of an insoluble phase containing alkaline matter has evidently gone unnoticed, for comments concerning its existence in the patents of biodiesel manufacturers are conspicuous by their absence. One likely reason is that no one is looking inside metal containers or pipes. Further evidence that this condition has gone unnoticed is that all the prior art centrifuge technology teaches (if at all) time G-force products appropriate only to the gross separation of the more dense glycerin phase from the less dense oil-phase, which may easily be accomplished in a continuous-flow system by means as low tech as a cyclonic separator.

The discovery of this transient phase, the small amount of settling in the first tens of hours, and the subsequent gradual clarification essentially simultaneously through the entire height of a 1000 ml graduated cylinder, was a discovery that could only have been made in transparent laboratory-ware, not metal production equipment. Still, this transient condition is again conspicuous by its absence from the published papers of scientists such as Vincente (*Bioresource Technology* 92 (2004) 297 305), who have published the results of their experiments conducted in small-scale experiments using laboratory glassware. The later bulk clarification has probably been mistaken for settling of the insoluble glycerin phase. This discovery opens the door to a continuous-flow manufacturing process, the key components of which are seen to be the presence of a centrifugal process with a particularly high range of time-G-force distance, and the absence of a water-washing step or a sorbent treatment procedure.

We claim:

1. A method for the production of biofuel, the method comprising:
    providing a first chemical mixture that comprises a basic catalyst and an alcohol;
    providing an essentially pure triglyceride;
    heating the essentially pure triglyceride;
    mixing in a high shear mixer the first chemical mixture with the heated essentially pure triglyceride to produce a heated second chemical mixture, wherein within the high shear mixer the heated second chemical mixture is raised from essentially atmospheric pressure to a higher pressure such that the material exiting the high shear mixer comprises fatty acid methyl esters, glycerin, alcohol, catalyst and undesired matter;
    passing the material comprising fatty acid methyl esters, glycerin, alcohol, catalyst and undesired matter through a cooling chamber;
    centrifuging the material comprising fatty acid methyl esters, glycerin, alcohol, catalyst and undesired matter with
        a cyclonic separator to remove glycerin, and
        a high speed separator to remove catalyst, wherein the centrifuging with the high speed separator is performed at greater than 6000 Gs,
    to produce a material consisting essentially of fatty acid methyl esters, alcohol and undesired matter;
    removing alcohol from the material consisting essentially of fatty acid methyl esters, alcohol and undesired matter to produce a material consisting essentially of fatty acid methyl esters and undesired matter;
    heating the material consisting essentially of fatty acid methyl esters and undesired matter to a distillation temperature;
    distilling the material consisting essentially of fatty acid methyl esters and undesired matter at a pressure less than atmospheric pressure to produce a vapor consisting essentially of fatty acid methyl esters; and
    condensing the vapor consisting essentially of fatty acid methyl esters to provide a liquid, wherein the liquid is the biofuel.

2. The method of claim 1, wherein the environment for the method for the production of biofuel is an inert environment.

3. The method of claim 1, wherein the method for production of biofuel does not include the addition of water.

4. The method of claim 1, wherein the centrifuging with the high speed separator is performed for approximately one minute per 90 mm of radial separation distance.

5. The method of claim 1, wherein the distilling is performed at a pressure of about a tenth of an atmosphere.

6. A method for the production of biofuel, the method comprising:
    providing an alcohol and a basic catalyst;
    providing an animal-based oil and/or a vegetable-based oil;
    mixing in a high shear mixer the alcohol and catalyst with the oil to produce a first chemical mixture comprising fatty acid methyl esters, glycerin, alcohol, catalyst and undesired matter, wherein during mixing the mixture is raised from essentially atmospheric pressure to a higher pressure;
    passing the first chemical mixture through a cooling chamber;
    centrifuging the first chemical mixture with a cyclonic separator to remove glycerin and with a high speed separator to remove catalyst, to produce a material consisting essentially of fatty acid methyl esters, alcohol and undesired matter, wherein the centrifuging with the high speed separator is performed at greater than 6000 Gs;
    removing alcohol from the material consisting essentially of fatty acid methyl esters, alcohol and undesired matter to produce a material consisting essentially of fatty acid methyl esters and undesired matter;
    heating the material consisting essentially of fatty acid methyl esters and undesired matter to a distillation temperature;
    distilling the material consisting essentially of fatty acid methyl esters and undesired matter at a pressure less than atmospheric pressure to produce a vapor consisting essentially of fatty acid methyl esters; and condensing the vapor consisting essentially of fatty acid methyl esters to provide a liquid, wherein the liquid is the biofuel.

7. The method of claim 6 wherein the environment for the method for the production of biofuel is an inert environment.

8. The method of claim 6, wherein the method for production of biofuel does not include the addition of water.

9. The method of claim 6, wherein the centrifuging with the high speed separator is performed for approximately one minute per 90 mm of radial separation distance.

10. The method of claim 6, wherein the distilling is performed at a pressure of about one tenth of an atmosphere.

11. A method for the production of biofuel, the method comprising:
   providing a first chemical mixture that comprises a basic catalyst and an alcohol;
   providing a triglyceride;
   mixing in a high shear mixer the first chemical mixture with the triglyceride to produce a second chemical mixture comprising fatty acid methyl esters, glycerin, alcohol, catalyst and undesired matter, wherein during mixing the second chemical mixture is raised from essentially atmospheric pressure to a higher pressure;
   passing the second chemical mixture through a cooling chamber;
   centrifuging the material comprising fatty acid methyl esters, glycerin, alcohol, catalyst and undesired matter with
      a cyclonic separator to remove glycerin, and
      a high speed separator to remove catalyst, wherein the centrifuging with the high speed separator is performed at greater than 6000 Gs,
   to produce a material consisting essentially of fatty acid methyl esters, alcohol and undesired matter;
   removing alcohol from the material consisting essentially of fatty acid methyl esters, alcohol and undesired matter to produce a material consisting essentially of fatty acid methyl esters and undesired matter;
   heating the material consisting essentially of fatty acid methyl esters and undesired matter to a distillation temperature;
   distilling the material consisting essentially of fatty acid methyl esters and undesired matter at a pressure less than atmospheric pressure to produce a vapor consisting essentially of fatty acid methyl esters; and
   condensing the vapor consisting essentially of fatty acid methyl esters to provide a liquid, wherein the liquid is the biofuel.

* * * * *